United States Patent [19]

Luk et al.

[11] Patent Number: 5,243,042
[45] Date of Patent: Sep. 7, 1993

[54] 1-THIAGUANOSINE AND PROCESS FOR PREPARING OXANOSINE AND 1-THIAGUANOSINE

[75] Inventors: Kin-Chun Luk, North Caldwell; Dennis D. Keith, Montclair, both of N.J.

[73] Assignee: Hoffmann-La Roche Inc., Nutley, N.J.

[21] Appl. No.: 561,628

[22] Filed: Aug. 2, 1990

[51] Int. Cl.⁵ .............................................. C07H 19/00
[52] U.S. Cl. ............................... 536/27.13; 536/27.81; 536/28.8
[58] Field of Search .................. 536/24, 27.13, 26.14, 536/124; 514/45, 46

[56] References Cited

U.S. PATENT DOCUMENTS

| | | | |
|---|---|---|---|
| 3,917,583 | 11/1975 | Meyer et al. | 536/29 |
| 4,530,998 | 7/1985 | Umezawa et al. | 536/24 |
| 4,946,846 | 8/1990 | Nomura et al. | 544/279 |

FOREIGN PATENT DOCUMENTS

0114331 12/1983 European Pat. Off. ............. 514/43

OTHER PUBLICATIONS

Yagisawa et al., Tetrahedron Letters, vol. 24, No. 9, pp. 931–932 (1983).
Yagisawa et al., A Facile Total Synthesis of Oxanosine, A Novel Nucleoside Antibiotic, 24 Tet. Let. 931–32 (1983).
Kaneko et al., Reactions of 1-(2-Acetoxyethoxy)methyl-5-amino-4-cyanoimidazole with Isothiocyanates, 36 Chem. Pharm. Bull. 1283–88 (1988).

*Primary Examiner*—Johnnie R. Brown
*Assistant Examiner*—J. Oliver Wilson
*Attorney, Agent, or Firm*—George M. Gould; George W. Johnston; William Krovatin

[57] ABSTRACT

The invention relates to antibacterially active 5-amino-3-($\beta$-D-ribofuranosyl)imidazo[4,5-d][1,3]thiazin-7(3H)-one, also referred to as 1-thiaguanosine, a composition and method comprising the same and processes and intermediates for the preparation of 1-thiaguanosine and 5-amino-3-($\beta$-D-ribofuranosyl)imidazo[4,5-d][1,3]oxazin-7(3H)-one, also referred to as oxanosine, a known compound.

14 Claims, No Drawings

1-THIAGUANOSINE AND PROCESS FOR PREPARING OXANOSINE AND 1-THIAGUANOSINE

BRIEF SUMMARY OF THE INVENTION

The invention relates to antibacterially active 5-amino-3-(β-D-ribofuranosyl)imidazo[4,5-d][1,3]thiazin-7(3H)-one, also referred to as 1-thiaguanosine, a composition and method comprising the same and processes and intermediates for the preparation of 1-thiaguanosine and 5-amino-3-(β-D-ribofuranosyl)imidazo[4,5-d][1,3]oxazin-7(3H)-one, also referred to as oxanosine, a known compound.

BACKGROUND OF THE INVENTION

Oxanosine is a known compound which has been isolated from *Streptomyces capreolus* MG 265-CF3. Oxanosine has been described as having antibacterial and carcinostatic activity and as an agent for treating tumors and bacterial diseases.

DETAILED DESCRIPTION OF THE INVENTION

The invention relates to 5-amino-3-(β-D-ribofuranosyl)-imidazo[4,5-d][1,3]thiazin-7(3H)-one, (1-thiaguanosine), which is useful as an antibacterial agent, and a method and compositions comprising said compound.

The process for preparing 1-thiaguanosine, which can also be characterized by the formula

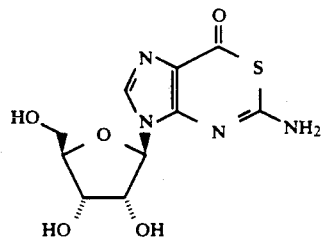

Ia and 5-amino-3-(β-D-ribofuranosyl)imidazo[4,5-d][1,3]oxazin-7(3H)-one, (oxanosine), can be carried out as set forth in Reaction Scheme I, which follows.

REACTION SCHEME I

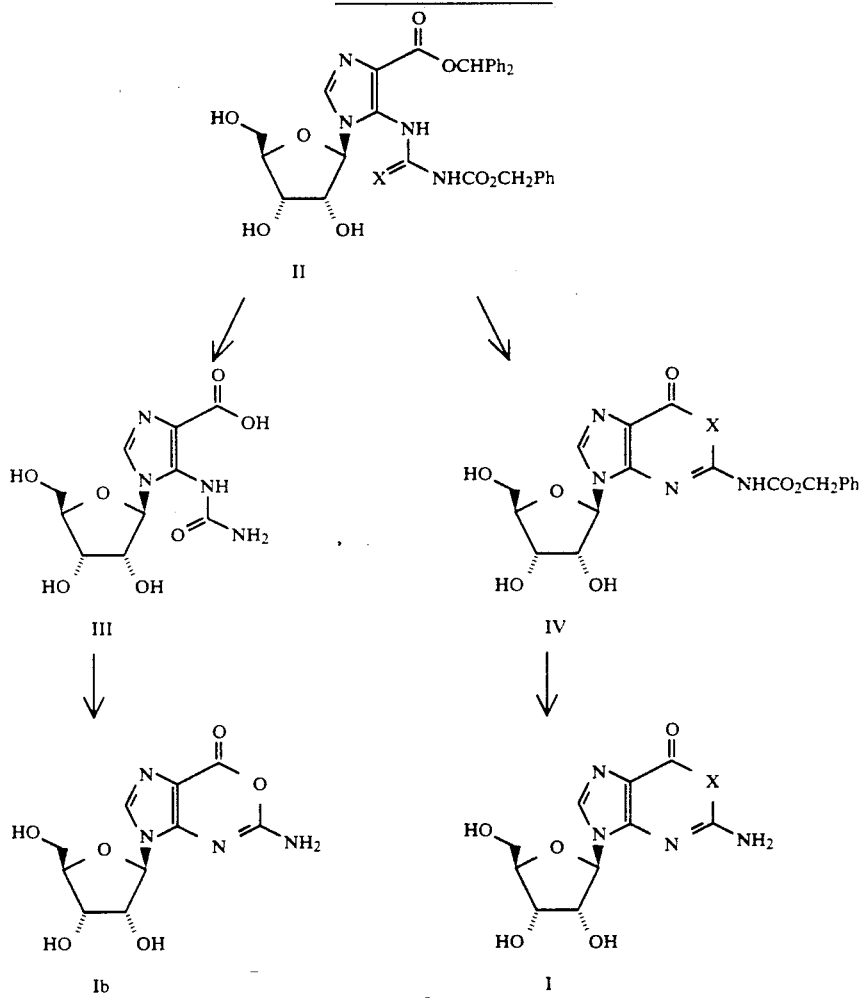

wherein X can be oxygen (O) or sulfur (S).

It is noted that when X is S, the compounds can be characterized as compounds of formula Ia, IIa and IVa, respectively, and when X is O, the compounds can be characterized as compounds of formulas Ib, IIb and IVb, respectively.

In Reaction Scheme I, a compound of formula II, wherein X is O, the preparation of which is hereinafter described in Reaction Scheme II, is hydrogenated with 10% palladium on carbon under hydrogen pressure in the presence of a solvent, for example, dimethylformamide, tetrahydrofuran, an alkanol such as ethanol, or the like, to yield the compound of formula III.

The resulting compound of formula III can be cyclized by treatment with a carbodiimide such as dicyclohexylcarbodiimide (DCC), 1-(3-dimethylaminopropyl)-3-ethylcarbodiimide hydrochloride or the like, to yield the corresponding compound of formula I wherein X is O.

Alternatively, a compound of formula II, wherein X is O or S, is, as a first step, selectively hydrolyzed by treatment with an acid such as trifluoroacetic acid, in an organic solvent, for example, a chlorinated hydrocarbon such as dichloromethane, or dimethylsulfoxide, dimethylformamide, a ketone such as acetone, an ester such as ethylacetate, or an ether such as tetrahydrofuran, preferably at room temperature, and the resulting mixture is then treated with a carbodiimide such as dicyclohexylcarbodiimide, 1-(3-dimethylaminopropyl)-3-ethylcarbodiimide hydrochloride or the like, to yield the corresponding compound of formula IV.

A compound of formula IV is hydrogenated with 10% palladium on carbon under hydrogen pressure in the presence of a solvent, for example, dimethylformamide, an alkanol such as ethanol, or the like to yield the corresponding compound of formula I.

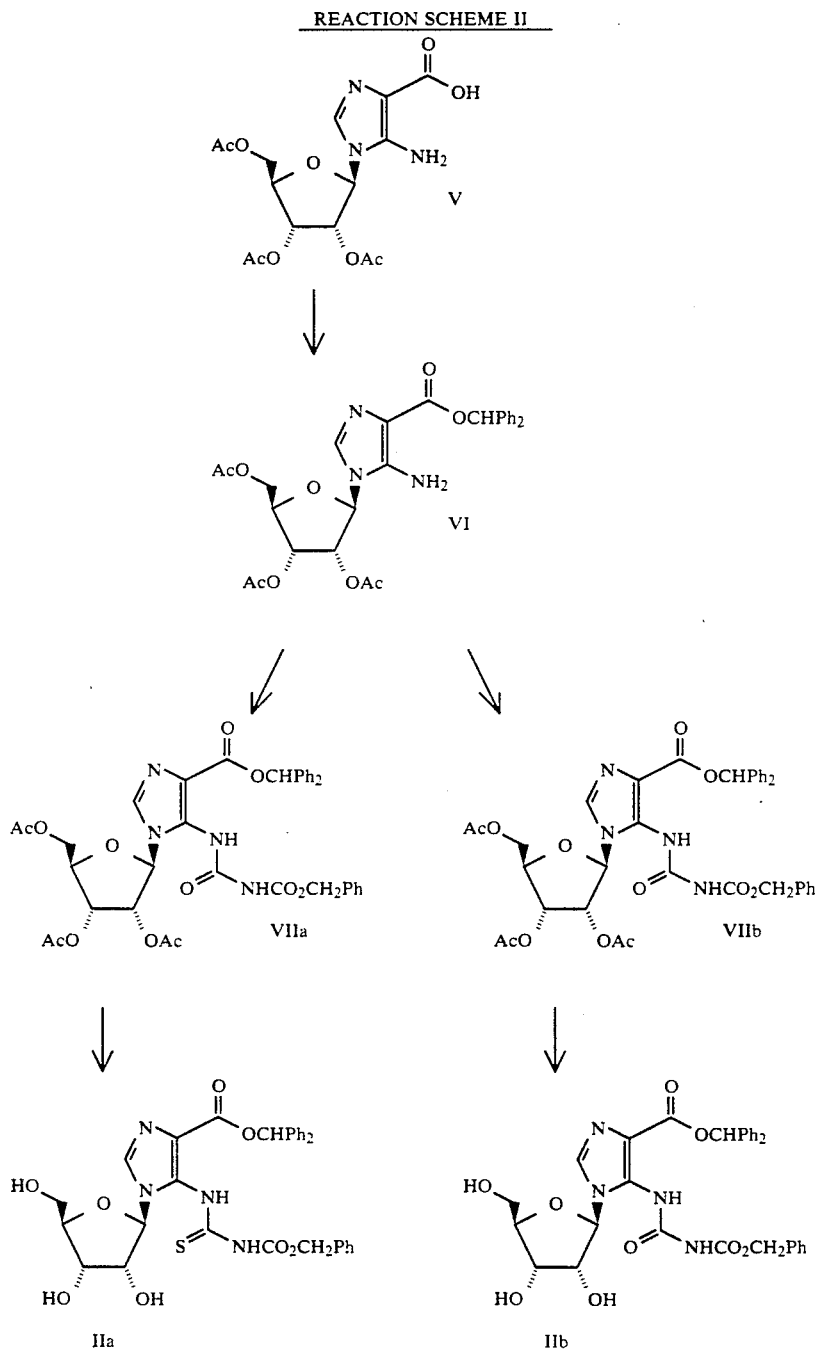

REACTION SCHEME II

In Reaction Scheme II, a compound of formula V, which is a known compound, is reacted with diphenyldiazomethane in an organic solvent, for example, a chlorinated hydrocarbon such as dichloromethane, or dimethylsulfoxide, dimethylformamide, a ketone such as acetone, an ester such as ethylacetate, or an ether such as tetrahydrofuran, preferably at room temperature, to yield the compound of formula VI.

The resulting compound of formula VI can be condensed with benzyloxycarbonyl isothiocyanate in an organic solvent, for example, a chlorinated hydrocarbon such as dichloromethane, or dimethylsulfoxide, dimethylformamide, a ketone such as acetone, an ester such as ethylacetate, or an ether such as tetrahydrofuran, preferably at room temperature to yield a compound of formula VIIa. To prepare a compound of formula VIIb the compound of formula VI is reacted with benzyloxycarbonyl isocyanate, at a temperature and in the presence of a solvent, as described above.

To obtain a compound of formula IIa or IIb, the compound of formula VIIa or VIIb, respectively, is hydrolyzed with an alkali metal hydroxide, in an alkanol such as methanol, and the resulting product is recovered by known procedures such as neutralization, chromatography or the like.

The compound of formula Ia, namely, 5-amino-3-($\beta$-D-ribofuranosyl)imidazo[4,5-d][1,3]thiazin-7(3H)-one, has antibacterial activity and, therefore, can be used as an antibacterial agent.

The antibacterial activity of the compound of formula Ia can be demonstrated by the minimum inhibitory concentration (MIC) to inhibit the growth of bacteria, which was determined by the agar dilution method[1]. To avoid possible antimetabolite reversal, a minimal agar medium[2] was employed. Inoculum was grown overnight at 36° C. in minimal broth medium and diluted a hundred-fold before use. Agar plates containing a serial dilution of the compounds of formula Ia were inoculated using a Steer's replicator. Approximately 3 $\mu$L was applied per spot. MICs were recorded after overnight incubation at 36° C.

[1] Barry, A. L., Procedure for Testing Antimicrobial Agents in Agar Media: Theoretical Considerations, p. 1-26. In Victor Lorian (Ed.), Antibiotics in Laboratory Medicine, 2nd ed. The Williams & Wilkins Co., Baltimore.
[2] Davis, B. D.; Mingioli, E. S. *J. BACTERIOL.* 1950, 60, 17-28.

The minimum inhibitory concentrations of 1-thiaguanosine, the compound of formula Ia, against various bacteria were as follows:

| MIC VALUES ($\mu$g/mL) | |
|---|---|
| E. coli 257 | 16 |
| E. coli ATCC 25922 | 128 |
| E. coli B | 128 |
| E. coli 94 | 32 |
| E. coli 2721B | 128 |
| Prov. rettgeri ATTC 9250 | 4 |
| S. typhimurium LT-2 | 8 |
| S. typhimurium ATTC 13311 | 8 |

The compound of the formula Ia can be used for the treatment and prophylaxis of bacterially caused infectious diseases. A daily dose of about 0.1 g to about 5 g can be utilized for the treatment of such infectious diseases in warm blooded mammals. Parenteral administration of the compound of formula Ia according to the invention is particularly preferred.

The compound of formula Ia can be used as medicament, for example, in the form of pharmaceutical preparations which contain it mixed with a pharmaceutical, organic or inorganic inert carrier material suitable for enteral or parenteral administration, such as, for example, water, gelatin, gum arabic, lactose, starch, magnesium stearate, talc, vegetable oils, polyalkylene glyclols, and the like. The pharmaceutical preparations can be in the solid form, for example, as enteric coated tablets, or capsules, dragees or suppositories or in the liquid form, for example, as solutions, parenteral solutions, suspensions or emulsions. If appropriate, it can be sterilized and/or contain adjuvants, such as preserving, stabilizing, wetting or emulsifying agents, salts for modifying the osmotic pressure, anesthetics or buffers. They can also additionally contain other therapeutically valuable substances. The compound of the formula Ia and its hydrates, can preferably be used for parenteral administration, and for this purpose are preferably made into preparations as lyophilisates or dry powders for dilution with customary agents, such as water or isotonic common salt solution.

The example which follow further describe the invention. All temperatures are given in degrees centigrade.

EXAMPLE 1

5-Amino-1-(2,3,5-tris-O-acetyl-$\beta$-D-ribofuranosyl)-1H-imidazole-4-carboxylic acid diphenylmethyl ester (Compound of formula VI)

Diphenyldiazomethane (2.0 g, 10.3 mmol) was added to the suspension of 5-amino-1-(2,3,5-tris-O-acetyl-$\beta$-D-ribofuranosyl)-1H-imidazole-4-carboxylic acid (3.86 g, 10 mmol) in CH$_2$Cl$_2$ (50 mL). The mixture was stirred at room temperature for 16 h, by which time all the reactants had dissolved. The reaction mixture was poured onto the top of a column of silica gel (100 g, packed in CH$_2$Cl$_2$, collected 100-mL fractions), and the column was washed with 5% EtOAc in CH$_2$Cl$_2$ (300 mL), then the product was eluted with 40% EtOAc in CH$_2$Cl$_2$. Fractions 5 to 10 were combined and concentrated, then pumped under high vacuum overnight to give 5-amino-1-(2,3,5-tris-O-acetyl-$\beta$-D-ribofuranosyl)-1H-imidazole-4-carboxylic acid diphenylmethyl ester as a pale yellow foam: 4.86 g (88% yield); IR (CHCl$_3$) 3445, 3345, 1752, and 1678 cm$^{-1}$; HRMS (EI) m/z found 551.1870 [calcd for C$_{28}$H$_{29}$N$_3$O$_9$, 551.1904 (M$^+$)]; NMR (CDCl$_3$) $\delta$2.13 (s, 9), 4.32 (d of d, 1,J=12 and 3 Hz), 4.40 (m, 1), 4.47 (d of d, 1,J=12 and 3 Hz), 5.30 (m, 1), 5.45 (t, 1, J=5 Hz), 5.48 (s, 2), 5.67 (d, 1, J=5 Hz), 7.08 (s, 1), 7.25 (m, 3), 7.32 (t, 4,J=7 Hz), UV max (CH$_3$OH) 267 nm ($\epsilon$12510).

EXAMPLE 2

5-[[[[(Phenylmethoxy)carbonyl]amino]carbonyl]amino]-1-($\beta$-D-ribofuranosyl-2,3,5-triacetate)-1H-imidazole-4-carboxylic acid diphenylmethyl ester (Compound of formula VIIIb)

5-Amino-1-(2,3,5-tris-O-acetyl-$\beta$-D-ribofuranosyl)-1H-imidazole-4-carboxylic acid diphenylmethyl ester (2.2 g, 4.0 mmol) was dissolved in dry ClCH$_2$CH$_2$Cl (30 mL). Benzyloxycarbonyl isocyanate (0.96 g, 5.4 mmol) in ClCH$_2$CH$_2$Cl (20 mL) was added and the mixture was stirred at room temperature for 30 minutes. The mixture was concentrated under reduced pressure and dried under high vaccum to give 5-[[[[(phenylmethoxy)carbonyl]amino]carbonyl]amino]-1-($\beta$-D-ribofuranosyl-2,3,5-triacetate)-1H-imidazole-4-carboxylic acid diphenylmethyl ester as a yellow foam: 2.90 g (quantitative yield). An analytically pure sample was obtained from 0.25 g of the foam by chromatography on silica gel (32 g) using 20% CH$_3$CN in CHCl$_3$ (v/v) as eluent. Fractions of 25 ml were collected. 5-[[[[(phenylmethoxy)carbonyl]amino]carbonyl]amino]-1-($\beta$-D-ribofuranosyl-2,3,5-triacetate)-1H-imidazole-4-carboxylic acid diphenylmethyl ester was eluted in fractions 7 through 12. These were combined, concentrated under reduced pressure and dried under high vacuum to give 188 mg of 5-[[[[(phenylmethoxy)carbonyl]amino]carbonyl]amino]-1-($\beta$-D-ribofuranosyl-2,3,5-triacetate)-1H-imidazole-4-carboxylic acid diphenylmethyl ester as a white foam: IR (CHCl$_3$) 3415, 3280, 1747, 1600, 1470, 1230, and 700 cm$^{-1}$; MS [(+)FAB]m/z 729 (M+H$^+$); NMR (CDCl$_3$) $\delta$2.05 (s, 3), 2.09 (s, 3), 2.13 (s, 3), 4.33 (t, 2, J=2.9 Hz), 4.37–439 (m, 1), 5.16 (s, 2), 5.23 (t, 1, J=5.4 Hz), 5.55 (t, 1, J=4.8 Hz), 5.90 (d, J=4.4 Hz), 7.17 (s, 1), 7.23–7.40 (m, 15), 7.81 (s, 1), 9.99 (s, 1); UV max (CH$_3$OH) 240 nm (sh, $\epsilon$9800) and 268 (infl, 1900).

EXAMPLE 3

5-[[[[(phenylmethoxy)carbonyl]amino]carbonyl]amino]-1-($\beta$-D-ribofuranosyl)-1H-imidazole-4-carboxylic acid diphenylmethyl ester (Compound of formula IIb)

Potassium hydroxide (0.41 g, 7.3 mmol) was added to a solution of 5-[[[[(phenylmethoxy)carbonyl]amino]carbonyl]amino]-1-($\beta$-D-ribofuranosyl-2,3,5-triacetate)-1H-imidazole-4-carboxylic acid diphenylmethyl ester (1.60 g, 2.2 mmol) in CH$_3$OH and the mixture was stirred at room temperature for 50 minutes. The mixture was then neutralized to pH 7 by addition of 2N HCl. Concentration under reduced pressure gave a viscous oil which was dissolved in CHCl$_3$ (50 mL) and washed with water (2×50 mL). The aqueous layers were extracted with CHCl$_3$ (50 mL). The organic layers were combined, dried (Na$_2$SO$_4$), concentrated under reduced pressure and dried under high vacuum to give 5-[[[[(phenylmethoxy)carbonyl]amino]carbonyl]amino]-1-($\beta$-D-ribofuranosyl)-1H-imidazole-4-carboxylic acid diphenylmethyl ester as a yellow foam: 1.34 g (100%); IR (KBr) 3440, 3270, 1720, 1590, 1490, 1230, and 690 cm$^{-1}$; MS [(+) FAB]m/z 603 (M+H$^+$), 625 (M+Na$^+$); NMR (Me$_2$SO-d$_6$) $\delta$3.36–3.69 (m, 2), 3.89 (m, 1), 4.05 (d, 1, J=4.1 Hz), 4.16 (d, 1, J=4.1 Hz), 5.07 (t, 1, J=4.1 Hz), 5.15–5.17 (m, 3), 5.48–5.50 (m, 2), 6.92 (s, 1), 7.21–7.43 (m, 15), 8.11 (s, 1), 9.53 (s, 1), 10.75 (s, 1); UV max (CH$_3$OH) 238 nm ($\epsilon$8300).

EXAMPLE 4

5-[[(phenylmethoxy)carbonyl]amino]-3-($\beta$-D-ribofuranosyl)imidazo[4,5-d][1,3]oxazin-7(1H)-one (Compound of formula IVb)

Trifluoroacetic acid (14 mL) was added to a solution of 5-[[[[(phenylmethoxy)carbonyl]amino]carbonyl]amino]-1-($\beta$-D-ribofuranosyl)-1H-imidazole-4-carboxylic acid diphenylmethyl ester (4.71 g, 7.8 mmol) in CH$_2$Cl$_2$ (60 mL) and anisole (14 mL) and the mixture was stirred at room temperature for 45 minutes. After concentrating the mixture under reduced pressure, toluene was added and evaporated under reduced pressure (2×50 mL) to give a yellow viscous oil which was dried under high vacuum to give 3.0 g of yellow solid. This yellow solid (1.0 g) was dissolved in N,N-dimethylformamide (1.5 mL, DMF) under an argon atmosphere. DCC (1.42 g) was suspended in EtOAc (4 mL) and added to the DMF solution with cooling in an ice-water bath. This mixture was stirred at ice-water bath temperature for 4 h. After filtration through sintered glass, the filtrate was added slowly to 20% ethyl ether in hexane (250 mL). A viscous oil resulted. The supernatant was decanted and concentrated under reduced pressure to about 75 mL. A second batch of product, again as a viscous oil, was obtained by decanting the supernatant. The oils thus obtained were dissolved in CH$_3$OH and adsorbed onto silica gel (5 g). The adsorbed material was dried under reduced pressure and loaded onto a column of silica gel (100 g) packed in 10% CH$_3$OH in CHCl$_3$ (v/v). Pure 5-[[(phenylmethoxy)carbonyl]amino]-3-($\beta$-D-ribofuranosyl)imidazo[4,5-d][1,3]oxazin-7(1H)-one was eluted with 10% CH$_3$OH in CHCl$_3$ (v/v, 100-mL fractions) in fractions 4 through 11. These fractions were combined, concentrated under reduced pressure and dried under high vacuum to give 5-[[(phenylmethoxy)carbonyl]amino]-3-($\beta$-D-ribofuranosyl)imidazo[4,5-d][1,3]oxazin-7(1H)-one as a white powder: 0.30 g, (33%); [$\alpha$]$^{25}_D$—7.56° (c 0.5, DMF); IR (KBr) 3424, 1818, 1772, 1570, and 701 cm$^{-1}$; MS [(+) FAB]m/z 419 (M+H$^+$); NMR (Me$_2$SO-d$_6$) $\delta$3.52–3.65 (m, 2), 3.91 (d, 1, J=3.5 Hz), 4.13–4.16 (m, 1), 4.47–4.51 (m, 1), 4.99 (t, 1, J=5.5 Hz), 5.21–5.23 (m, 3), 5.50 (d, 1, J=6.0 Hz), 5.73 (d, 1, J=5.9 Hz), 7.35–7.45 (m, 5), 8.27 (s, 1), 11.55 (s, 1); UV max (CH$_3$OH) 208 nm ($\epsilon$24500), 240 (infl, 10400), 246 (11850), 254 (sh 9960), 285 (10200).

Anal. Calcd for C$_{18}$H$_{18}$N$_4$O$_8$: C, 51.67; H, 4.34; N, 13.39. Found: C, 51.28; H, 4.33; N, 13.15.

EXAMPLE 5

Oxanosine from 5-[[(phenylmethoxy)carbonyl]amino]-3-($\beta$-D-ribofuranosyl)imidazo[4,5-d][1,3]oxazin-7(1H)-one 10% Palladium on charcoal (172 mg) was added to a solution of 5-[[(phenylmethoxy)carbonyl]amino]-3-($\beta$-D-ribofuranosyl)imidazo[4,5-d][1,3]oxazin-7(1H)-one (172 mg, 0.41 mmol) in DMF (7 mL) and the mixture was stirred at room temperature under a hydrogen atmosphere for 4 h. The mixture was filtered through prewashed Celite and was concentrated under high vacuum. The residue was dissolved in water and filtered through a Millipore Millex-HV filter (0.45 $\mu$m). The filtrate was lyophilized to give oxanosine as a white powder: 115 mg, (100%). Crystallization from warm water gave oxanosine (75%) as colorless needles: mp 191°–192° C.; [$\alpha$]$^{25}_D$—38.7° (c 1, H$_2$O); IR (KBr) 3440–3200, 1802, 1772, and 1550 cm$^{-1}$; MS [(+) FAB]m/z 285 (M+H$^+$); NMR (D$_2$O) $\delta$3.80–3.91 (m, 2), 4.21–4.23 (m, 1), 4.40 (t, 1, J=4.6 Hz), 4.69 (t, 1, J=5.5 Hz), 5.80–5.85 (d, 1, J=5.5 Hz), 7.98 (s, 1); UV max (H$_2$O) 245 nm ($\epsilon$11760), 287 (8450).

Anal Calcd for C$_{10}$H$_{12}$N$_4$O$_6$ (with 1.19% H$_2$O by Karl-Fischer titration): C, 41.75; H, 4.34; N, 19.50. Found: C, 41.58; H, 4.24; N, 19.48.

EXAMPLE 6

5-[[(Amino)carbonyl]amino]-1-($\beta$-D-ribofuranosyl)-1H-imidazole-4-carboxylic acid (Compound of formula III)

5-[[[[(phenylmethoxy)carbonyl]amino]carbonyl]amino]-1-($\beta$-D-ribofuranosyl)-1H-imidazole-4-carboxylic acid diphenylmethyl ester (1.76 g, 2.9 mmol) was dissolved in the mixture of DMF (50 mL), THF (20 mL) and ethanol (30 mL) and mixed with 10% palladium on charcoal. The mixture was hydrogenated at 50 psig pressure for 2 h. The catalyst was removed by filtration through Celite, and washed extensively with DMF and ethanol. Combined washing and filtrate was concentrated under reduced pressure to dryness. Residue was dissolved in 30% aqueous ethanol and filtered through a C18-Sep-Pak to remove the last traces of catalyst. This eluate was concentrated to dryness and partitioned between water (100 mL) and ether (2×100 mL). The aqueous layer was concentrated to dryness, redissolved in water and evaporated again and pumped under high vacuum to give 5-[[(amino)carbonyl]amino]-1-($\beta$-D-ribofuranosyl)-1H-imidazole-4-carboxylic acid as a colorless glass: yield 0.64 g (73%); IR (KBr) 3340, 1692 cm$^{-1}$; NMR (Me$_2$SO-d$_6$) $\delta$3.72–3.53 (m, 2), 3.84 (d, 1, J=4.3 Hz), 4.05 (s, 1), 4.14 (s, 1), 5.05 (s, 1), 5.11 (s, 1), 5.34 (s, 1), 5.50 (d, 1, J=4.3 Hz), 6.28 (s, 2), 7.92 (s, 1), 8.07 (s, 1); UV max (H$_2$O) 215 nm ($\epsilon$5800).

EXAMPLE 7

Oxanosine
(5-Amino-3-$\beta$-D-ribofuranosylimidazo[4,5-d][1,3]oxazin-7(3H)-one) from
5-[[(Amino)carbonyl]amino-1-($\beta$-D-ribofuranosyl)-1H-imidazole-4-carboxylic acid 1-(3-Dimethylaminopropyl)-3-ethylcarbodiimide hydrochloride (78 mg, 0.41 mmol) was added to a solution of 5-[[(amino)carbonyl]amino-1-($\beta$-D-ribofuranosyl)-1H-imidazole-4-carboxylic acid (19 mg, 0.063 mmol) in water (2 mL) and CH$_3$OH (5 mL) and the mixture was stirred at room temperature overnight. The reaction was quenched by addition of excess 60% aqueous acetic acid. After 30 minutes, the mixture was diluted with water, concentrated to remove CH$_3$OH and lyophilized. The resulting powder (100 mg) was chromatographed on reverse phase silica gel [10 g, flash, stepwise gradient elution: water (200 mL), 10% CH$_3$OH in water (v/v, 100 mL), 20% CH$_3$OH in water (v/v, 100 mL), 10-mL fractions]. Fractions containing the product were combined, concentrated under reduced pressure and lyophilized to give oxanosine: 16 mg (89%).

EXAMPLE 8

1-(2,3,5-tri-O-Acetyl-$\beta$-D-ribofuranosyl)-5-[[[[(phenylmethoxy)carbonyl]amino]thioxomethyl]amino]-1H-imidazole-4-carboxylic acid diphenylmethyl ester (Compound of formula VIIa)

Four portions of benzyloxycarbonyl isothiocyanate (Caution: stench, handle in a well ventilated hood only, crude, 2.0 g each, total 41 mmol) were added to a solution of 5-amino-1-(2,3,5-tris-O-acetyl-$\beta$-D-ribofuranosyl)-1H-imidazole-4-carboxylic acid diphenylmethyl ester (1.1 g, 2 mmol) in CH$_2$Cl$_2$ (10 mL) at 0 h, 6 h, 22 h and 30 h. The reaction mixture was stirred at room temperature under an argon atmosphere for a total of 46 h after the addition of the first portion of benzyloxycarbonyl isothiocyanate, then chromatographed on silica gel (100 g, column packed in CH$_2$Cl$_2$, 100-mL fractions), with CH$_2$Cl$_2$ (100 mL), followed by 25% EtOAc in CH$_2$Cl$_2$ as the eluant. Fractions 6 to 11 were combined, concentrated, and pumped under reduced pressure to give 1-(2,3,5-tri-O-acetyl-$\beta$-D-ribofuranosyl)-5-[[[[(phenylmethoxy)carbonyl]amino]-thioxomethyl]amino]-1H-imidazole-4-carboxylic acid diphenylmethyl ester as a pale yellow foam: 1.46 g (98% yield); IR (CHCl$_3$) 3405, 3250, 3200, 1750, 1738, 1600, and 1505 cm$^{-1}$; HRMS [(+) FAB] m/z found 767.2060 [calcd for C$_{37}$H$_{36}$N$_4$NaO$_{11}$S, 767.1999 (M+Na$^+$)], 745.2297 [calcd for C$_{37}$H$_{37}$N$_4$O$_{11}$S, 745.2180 (M+H$^+$)]; NMR (CDCl$_3$)$\delta$2.04 (s, 3), 2.10 (s, 3), 2.13 (s, 3), 4.33 (m, 2), 4.39 (m, 1), 5.10 (s, 2), 5.35 (m, 1), 5.52 (m, 1), 5.87 (m, 1), 7.10 (s, 1), 7.32 (m, 15), 7.87 (s, 1), 8.16 (s, 1), 10.95 (s, 1); UV max (95% C$_2$H$_5$OH) 215 nm (sh, $\epsilon$35000), 266 (13850).

EXAMPLE 9

5-[[(Phenylmethoxy)carbonyl](aminothioxomethylamino)]-1-($\beta$-D-ribofuranosyl)-1H-imidazole-4-carboxylic acid diphenylmethyl ester (Compound of formula IIa)

Potassium hydroxide (0.6 g, 10.7 mmol) in water (12 mL) was added to the solution of 1-(2,3,5-tri-O-acetyl-$\beta$-D-ribofuranosyl)-5-[[[[(phenylmethoxy)carbonyl]amino]thioxomethyl]amino]-1H-imidazole-4-carboxylic acid diphenylmethyl ester (1.46 g, 1.96 mmol) in a mixture of 2-propanol (25 mL) and dioxane (10 mL). After stirring at room temperature for 1 h, the reaction mixture was neutralized with 1N aqueous hydrochloric acid to pH 7. The solution was concentrated under reduced pressure to dryness, and the residue was then dissolved in CH$_3$OH and mixed with silica gel (10 g). Solvent was again evaporated off. The resulting silica gel was loaded on top of a silica gel column (100 g) packed in and eluted with CHCl$_3$—CH$_3$OH mixture, 9:1, v/v, (100-mL fractions). Fractions 4 to 8 were combined and concentrated, then pumped under reduced pressure, to give pure 5-[[(phenylmethoxy)carbonyl]-(aminothioxomethylamino)]-1-($\beta$-D-ribofuranosyl)-1H-imidazole-4-carboxylic acid diphenylmethyl ester as a white foam: 0.96 g (79% yield); IR (KBr) 3400, 1722, and 1495 cm$^{-1}$; HRMS [(+) FAB] m/z found 619.1892 [calcd for C$_{31}$H$_{31}$N$_4$O$_8$S, 619.1863 (M+H$^+$)], 620.1916 [calcd for C$_{30}$$^{13}$CH$_{31}$N$_4$O$_8$S, 620.1896 (M+H$^+$)]; NMR (Me$_2$SO-d$_6$)$\delta$3.57 (m, 1), 3.71 (m, 1), 3.89 (m, 1), 4.07 (m, 1), 4.22 (m, 1), 5.12 (m, 2), 5.17 (s, 2), 5.46 (d, 1, J=3 Hz), 5.50 (br s, 1), 6.88 (s, 1), 7.25 (m, 6), 7.40 (m, 9), 8.13 (s, 1), 11.06 (br s, 1), 11.87 (br s, 1); UV max (95% C$_2$H$_5$OH) 215 nm (sh, $\epsilon$28500), 265 (12000).

EXAMPLE 10

[3,7-Dihydro-7-oxo-3-($\beta$-D-ribofuranosyl)imidazo[4,5-d][1,3]thiazin-5-yl]carbamic acid phenylmethyl ester) (Compound of formula IVa)

5-[[(Phenylmethoxy)carbonyl](aminothioxomethylamino)]-1-($\beta$-D-ribofuranosyl)-1H-imidazole-4-carboxylic acid diphenylmethyl ester (0.31 g, 0.5 mmol) was dissolved in the mixture of trifluoroacetic acid (1 mL), anisole (1 mL), and CH$_2$Cl$_2$ (4 mL), and stirred magnetically at room temperature for 1 h. Solvent was evaporated off under reduced pressure. The residue was suspended in toluene (60 mL) and then concentrated. This was repeated with a second portion of toluene (60 mL). The resulting white solid was dissolved in dry DMF (5 mL). DCC (0.15 g, 0.7 mmol) was added, and mixture was stirred magnetically at room temperature for 5 h. A second portion of DCC (0.2 g, 1.0 mmol) was then added and mixture stirred for an additional 16 h. The precipitate was removed by filtration, washed with CH$_3$OH (5 mL), and the combined washing and filtrate was concentrated. The residue was dissolved in CH$_3$OH, mixed with silica gel (3.0 g) and evaporated to dryness. This silica gel sample was loaded on top of a silica gel column (30 g) packed in CHCl$_3$—CH$_3$OH mixture, (9:1, v/v), and eluted with the same solvent (400 mL), followed by a CHCl$_3$—CH$_3$OH mixture, (4:1, v/v, 250 mL), and collected 30-mL fractions. Fractions 8 to 14 were combined and concentrated, and pumped under reduced pressure to give pure [3,7-dihydro-7-oxo-3-(β-D-ribofuranosyl)imidazo[4,5-d][1,3]thiazin-5-yl]carbamic acid phenylmethyl ester) 0.14 g (64%). [3,7-Dihydro-7-oxo-3-(β-D-ribofuranosyl)imidazo[4,5-d][1,3]thiazin-5-yl]carbamic acid phenylmethyl ester was further purified by crystallization from CH$_3$OH to give needles (crystals contained one mole of CH$_3$OH of crystallization as determined by NMR): mp 194°–198° C.; IR (KBr) 3375, 1730, 1668, and 1532 cm$^{-1}$; HRMS [(+) FAB] m/z found 457.0776 [calcd for C$_{18}$H$_{18}$N$_4$NaO$_7$S, 457.0794 (M+Na$^+$)], 435.0997 [calcd for C$_{18}$H$_{19}$N$_4$O$_7$S, 435.0975 (M+H$^+$)]; NMR (Me$_2$SO-d$_6$) δ3.17 (d, 3, J=5 Hz), 3.55 (m, 1), 3.63 (m, 1), 3.89 (q, 1, J=5 Hz), 4.09 (q, 1, J=5 Hz), 4.13 (m, 1), 4.50 (q, 1, J=5 Hz), 5.03 (t, 1, J=5 Hz), 5.18 (d, 1, J=4 Hz), 5.22 (s, 2), 5.47 (d, 1, J=5 Hz), 5.90 (d, 1, J=6 Hz), 7.40 (m, 5), 8.36 (s, 1), 12.20 (s, 1); UV max (95% C$_2$H$_5$OH) 216 nm (ε31300), 223 (sh, 29500), 257 (6400), 265 (7940), 273 (sh, 7000), 315 (sh, 6800), 323 (7500), 340 (5100); (0.1N HCl) 218 nm (ε27850), 266 (9000), 275 (7600), 317 (7360); (pH 7) 216 nm (ε26120), 226 (26580), 266 (8450), 275 (8620), 290 (sh, 5300), 325 (7500), 335 (sh, 7200); (pH 11) 216 nm (ε22780), 230 (22780), 281 (14380), 290 (sh, 11380), 343 (11840).

EXAMPLE 11

1-Thiaguanosine
(5-Amino-3-(β-D-ribofuranosyl)imidazo[4,5-d][1,3]thiazin-7-(3H)-one)

A solution of [3,7-dihydro-7-oxo-3-(β-D-ribofuranosyl)imidazo[4,5-d][1,3]thiazin-5-yl]carbamic acid phenylmethyl ester (170 mg, 0.39 mmol) in dry DMF (10 mL) was hydrogenated in the presence of 10% palladium on charcoal (200 mg) at room temperature and 50 psig for 6 h. Additional catalyst (200 mg) was added and hydrogenation continued for another 16 h. Catalyst was removed by filtration and was washed with DMF (10 mL) and ethanol (10 mL). The washing and filtrate were combined and concentrated under reduced pressure. The residue was dissolved in CH$_3$OH and mixed with silica gel (3 g) and evaporated again to dryness. This silica gel sample was loaded on top of a silica gel column (30 g) packed in CHCl$_3$—CH$_3$OH mixture, 4:1, v/v, and eluted with the same solvent, collecting 30-mL fractions. Fractions 7 to 12 were combined and concentrated, and pumped under reduced pressure to give pure 1-thiaguanosine: 90 mg (53%). 1-Thiaguanosine was crystallized from water-ethanol mixture to give needles: mp 212°–215° C. (dec); IR (KBr) 3415, 3385, 3300, 3190, 3105, 1695, 1662, 1635, and 1530 cm$^{-1}$; HRMS [(+) FAB] m/z found 301.0597 [calcd for C$_{10}$H$_{13}$N$_4$O$_5$S, 301.0607 (M+H$^+$)]; NMR (Me$_2$SO-d$_6$) δ3.53 (m, 1), 3.60 (m, 1), 3.86 (q, 1, J=4 Hz), 4.09 (m, 1), 4.38 (m, 1), 5.03 (t, 1, J=5 Hz), 5.20 (m, 1), 5.48 (d, 1, J=5 Hz), 5.80 (d, 1, J=6 Hz), 8.11 (s, 1), 8.34 (s, 2); UV max (95% C$_2$H$_5$OH) 207 nm (ε26750), 218 (sh, 24375), 264 (8000), 274 (5750), 323 (6725); (0.1N HCl) 210 nm (ε19000), 266 (8450), 277 (sh, 6400), 325 (6600); (pH 7 and pH 11) 209 nm (ε18400), 220 (sh, 18200), 264 (7600), 275 (sh, 5200), 325 (6450).

EXAMPLE 12

| TABLET FORMULATION (Wet Granulation) | | | |
|---|---|---|---|
| | | mg/tablet | |
| Item | Ingredient | 100 mg | 500 mg | 1000 mg |
| 1. | 1-Thiaguanosine | 100 | 500 | 1000 |
| 2. | Lactose | 132 | — | — |
| 3. | Pregelatinized Starch | 16 | 30 | 50 |
| 4. | Modified Starch | 30 | 40 | 50 |
| 5. | Magnesium Stearate | 2 | 6 | 8 |
| | TOTAL | 280 | 576 | 1108 |

Manufacturing Procedure:
1. Mix Items 1, 2, 3 and 4 and granulate with water.
2. Dry the granulation at 50° C.
3. Pass the granulation through suitable milling equipment.
4. Add Item 5 and mix for three minutes; compress on a suitable press.

EXAMPLE 13

| CAPSULE FORMULATION | | | | | |
|---|---|---|---|---|---|
| | Ingredients | mg/capsule | | | |
| 1. | 1-Thiaguanosine | 25 | 50 | 100 | 500 |
| 2. | Lactose Hydrous | 143 | 168 | 148 | — |
| 3. | Corn Starch | 20 | 20 | 40 | 70 |
| 4. | Talc | 10 | 10 | 10 | 25 |
| 5. | Magnesium Stearate | 2 | 2 | 2 | 5 |
| | TOTAL | 200 | 250 | 300 | 600 |

Manufacturing Procedure:
1. Mix Items 1, 2 and 3 in a suitable mixer for 30 minutes.
2. Add Items 4 and 5 and mix for 3 minutes.
3. Fill into suitable capsules.

We claim:
1. The compound, 5-amino-3-(β-D-ribofuranosyl)-imidazo[4,5-d][1,3]thiazin-7(3H)-one.
2. A process for the preparation of a compound of the formula:

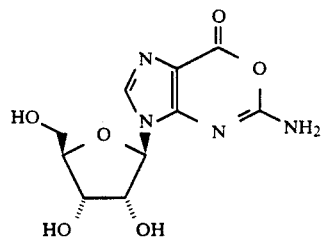

which comprises hydrogenating a compound of the formula

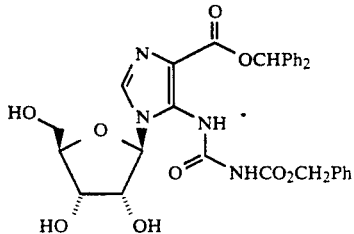

with hydrogen in the presence of a catalyst to yield a compound of the formula

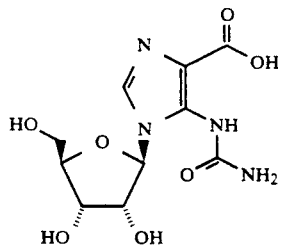

and, thereafter, cyclizing the compound of formula III with a carbodiimide to obtain the desired compound of formula Ib.

3. A process for the preparation of a compound of the formula

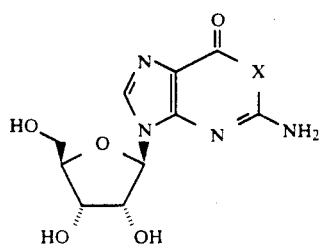

wherein X is S or O, which comprises selectively hydrolyzing a compound of the formula

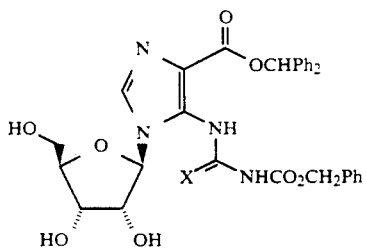

with an acid in an organic solvent and treating the resulting mixture with a carbodiimide to yield the corresponding compound of the formula

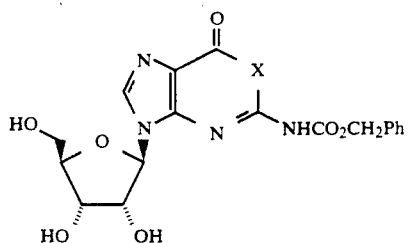

and, thereafter, hydrogenating the resulting compound of formula IV with hydrogen in the presence of a catalyst to obtain the corresponding compound of formula I.

4. A compound of the formula

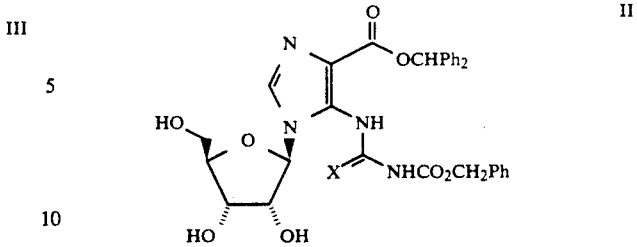

wherein X is S or O.

5. The compound, in accordance with claim 4, 5-[[[[(phenylmethoxy)carbonyl]amino]carbonyl]amino]-1-(β-D-ribofuranosyl)-1H-imidazole-4-carboxylic acid diphenylmethyl ester.

6. The compound, in accordance with claim 4, 5-[[(phenylmethoxy)carbonyl](aminothioxomethylamino)]-1-(β-D-ribofuranosyl)-1H-imidazole-4-carboxylic acid diphenylmethyl ester.

7. The compound, 5-[[(amino)carbonyl]amino]-1-(β-D-ribofuranosyl)-1H-imidazole-4-carboxylic acid.

8. A compound of the formula

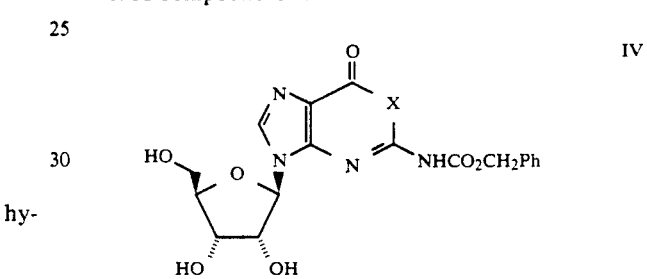

wherein X is S or O.

9. The compound, in accordance with claim 8, [3,7-dihydro-7-oxo-3-(β-D-ribofuranosyl)imidazo[4,5-d][1,3]thiazin-5-yl]carbamic acid phenylmethyl ester.

10. The compound, in accordance with claim 8, 5-[[(phenylmethoxy)carbonyl]amino]-3-(β-D-ribofuranosyl)imidazo[4,5-d][1,3]oxazin-7(1H)-one.

11. The compound, 5-amino-1-(2,3,5-tris-O-acetyl-β-D-ribofuranosyl)-1H-imidazole-4-carboxylic acid diphenylmethyl ester.

12. A compound of the formula

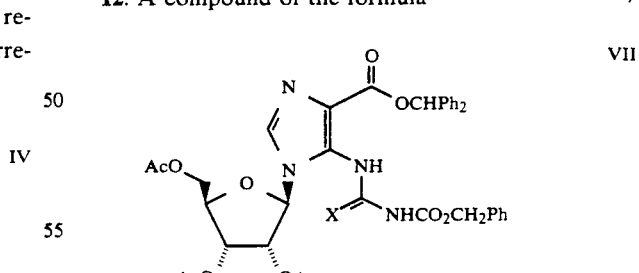

wherein Ac is CH₃CO- and X is S or O.

13. The compound, in accordance with claim 12, 1-(2,3,5-tri-O-acetyl-β-D-ribofuranosyl)-5-[[[[(phenylmethoxy)carbonyl]amino thioxomethyl]amino]-1H-imidazole-4-carboxylic acid diphenylmethyl ester.

14. The compound, in accordance with claim 12, 5-[[[[(phenylmethoxy)carbonyl]amino]carbonyl]amino]-1-(β-D-ribofuranosyl-2,3,5-triacetate)-1H-imidazole-4-carboxylic acid diphenylmethyl ester.

* * * * *